(12) United States Patent
Han et al.

(10) Patent No.: US 10,005,795 B1
(45) Date of Patent: Jun. 26, 2018

(54) GROUP 4 METAL ELEMENT-CONTAINING COMPOUND, METHOD OF PREPARING THE SAME, PRECURSOR COMPOSITION INCLUDING THE SAME FOR DEPOSITING FILM, AND METHOD OF DEPOSITING FILM USING THE SAME

(71) Applicant: UP CHEMICAL CO., LTD., Pyeongtaek-si, Gyeonggi-do (KR)

(72) Inventors: Won Seok Han, Pyeongtaek-si (KR); Wonyong Koh, Daejeon (KR); Myeong-Ho Park, Suwon-si (KR)

(73) Assignee: UP CHEMICAL CO., LTD., Pyeongtaek-si, Gyeonggi-do (KR)

( * ) Notice: Subject to any disclaimer, the term of this patent is extended or adjusted under 35 U.S.C. 154(b) by 0 days. days.

(21) Appl. No.: 15/577,913

(22) PCT Filed: Feb. 3, 2017

(86) PCT No.: PCT/KR2017/001161
§ 371 (c)(1),
(2) Date: Nov. 29, 2017

(87) PCT Pub. No.: WO2017/135715
PCT Pub. Date: Aug. 10, 2017

(30) Foreign Application Priority Data

Feb. 3, 2016 (KR) .................. 10-2016-0013203

(51) Int. Cl.
*C07F 7/00* (2006.01)
*C23C 16/455* (2006.01)
*C23C 16/18* (2006.01)
*C07F 7/28* (2006.01)

(52) U.S. Cl.
CPC .................. *C07F 7/00* (2013.01); *C07F 7/28* (2013.01); *C23C 16/18* (2013.01); *C23C 16/45553* (2013.01)

(58) Field of Classification Search
None
See application file for complete search history.

(56) References Cited

FOREIGN PATENT DOCUMENTS

| KR | 1020070121281 A | 12/2007 |
|---|---|---|
| KR | 100852234 B1 | 8/2008 |
| KR | 1020080101040 A | 11/2008 |
| KR | 1020100083145 A | 7/2010 |
| KR | 1020150139628 A | 12/2015 |
| KR | 1020160000392 A | 1/2016 |
| WO | 2015155214 A2 | 10/2015 |

OTHER PUBLICATIONS

International Search Report of PCT/KR2017/001161 dated May 4, 2017, 2 pages.

*Primary Examiner* — Clinton A Brooks
(74) *Attorney, Agent, or Firm* — Brundidge & Stanger, P.C.

(57) ABSTRACT

The present disclosure provides a Group 4 metal element-containing novel compound, a method of preparing the Group 4 metal element-containing compound, a precursor composition including the Group 4 metal element-containing compound for depositing a film, and a method of depositing a Group 4 metal element-containing film using the precursor composition.

10 Claims, 9 Drawing Sheets

GROUP 4 METAL ELEMENT-CONTAINING COMPOUND, METHOD OF PREPARING THE SAME, PRECURSOR COMPOSITION INCLUDING THE SAME FOR DEPOSITING FILM, AND METHOD OF DEPOSITING FILM USING THE SAME

CROSS-REFERENCE TO RELATED APPLICATIONS

This Application is the National Stage filing under 35 U.S.C. § 371 of PCT Application Ser. No. PCT/KR2017/001161 filed on Feb. 3, 2017, which claims the benefit under 35 U.S.C. § 119(a) of Korean Patent Application No. 10-2016-0013203 filed on Feb. 3, 2016. The entire disclosures of both applications are hereby incorporated herein by reference in their entireties.

TECHNICAL FIELD

The present disclosure relates to a Group 4 metal element-containing novel compound, a method of preparing the Group 4 metal element-containing compound, a precursor composition including the Group 4 metal element-containing compound for depositing a film, and a method of depositing a Group 4 metal element-containing film using the precursor composition.

BACKGROUND

A compound containing a Group 4 metal element such as Ti, Zr, and Hf, e.g., a film of an oxide or nitride containing a Group 4 metal element, e.g., a zirconium oxide film, a titanium nitride film, etc., is used as a high dielectric material, an electrode, etc. to manufacture a semiconductor device. To form a film containing a Group 4 metal element by chemical vapor deposition (CVD) or atomic layer deposition (ALD), various Group 4 metal compounds are used. Further, a compound containing a Group 4 metal element is also used as a catalyst for polymer synthesis [Korean Patent No. 10-0852234]. However, there is still a need for developing a Group 4 metal element-containing novel compound which can be usefully utilized as a precursor for forming a uniform film, particularly for forming a Group 4 metal element-containing uniform film or thin film on the entire surface of a substrate having a trench (groove) or porous substrate.

DISCLOSURE OF THE INVENTION

Problems to be Solved by the Invention

The present disclosure is conceived to provide a Group 4 metal element-containing novel compound, a method of preparing the Group 4 metal element-containing compound, a precursor composition including the Group 4 metal element-containing compound for depositing a film, and a method of depositing a Group 4 metal element-containing film using the precursor composition.

However, problems to be solved by the present disclosure are not limited to the above-described problems. Although not described herein, other problems to be solved by the present disclosure can be clearly understood by those skilled in the art from the following description.

Means for Solving the Problems

According to a first aspect of the present disclosure, there is provided a Group 4 metal element-containing compound, represented by the following Chemical Formula 1:

[Chemical Formula 1]

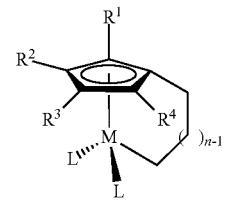

in the above Chemical Formula 1, M is Ti, Zr or Hf, L is $NR^5R^6$, $OR^7$ or a halogen, each of $R^1$ to $R^7$ is independently hydrogen or a linear or branched alkyl group having 1 to 4 carbon atoms, and n is an integer of from 1 to 3.

According to a second aspect of the present disclosure, there is provided a method of preparing a Group 4 metal element-containing compound, represented by the following Chemical Formula 1, including reacting a compound represented by $ML_4$ with a Grignard reagent:

[Chemical Formula 1]

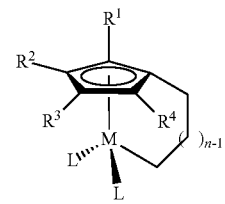

in the above Chemical Formula, M is Ti, Zr or Hf, L is $NR^5R^6$, $OR^7$ or a halogen, each of $R^1$ to $R^7$ is independently hydrogen or a linear or branched alkyl group having 1 to 4 carbon atoms, and n is an integer of from 1 to 3.

According to a third aspect of the present disclosure, there is provided a method of preparing a Group 4 metal element-containing compound, represented by the following Chemical Formula 1', including reacting a compound represented by the following Chemical Formula 4 with $M'NR^5R^6$ as an alkali metal salt of a dialkylamine or $M'OR^7$ as an alkali metal salt of an alcohol, wherein in each of the $M'NR^5R^6$ and $M'OR^7$, M' is an alkali metal and each of $R^5$ to $R^7$ is independently hydrogen or a linear or branched alkyl group having 1 to 4 carbon atoms:

[Chemical Formula 4]

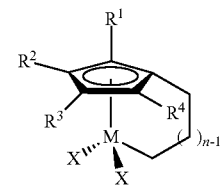

in the above Chemical Formula 4, M is Ti, Zr or Hf, each of R¹ to R⁴ is independently hydrogen or a linear or branched alkyl group having 1 to 4 carbon atoms, X is a halogen, and n is an integer of from 1 to 3;

[Chemical Formula 1']

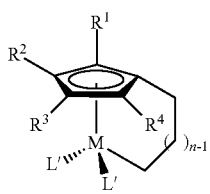

in the above Chemical Formula 1', M is Ti, Zr or Hf, L' is NR⁵R⁶ or OR⁷, each of R¹ to R⁷ is independently hydrogen or a linear or branched alkyl group having 1 to 4 carbon atoms, and n is an integer of from 1 to 3.

According to a fourth aspect of the present disclosure, there is provided a precursor composition for depositing a film, including a Group 4 metal element-containing compound according to the first aspect of the present disclosure.

According to a fifth aspect of the present disclosure, there is provided a method of depositing a Group 4 metal element-containing film, including forming a Group 4 metal element-containing film using a precursor composition for depositing a film according to the fourth aspect of the present disclosure.

Effects of the Invention

According to an exemplary embodiment of the present disclosure, a Group 4 metal element-containing novel compound has a structure in which a carbon directly bonded to a Group 4 central metal is connected to a cyclopentadienyl group coordinated at the central metal through an alkylene chain and is a novel compound which has not been conventionally known in the art. The Group 4 metal element-containing novel compounds according to an exemplary embodiment of the present disclosure have high thermal stability and thus can be used as a precursor for atomic layer deposition or chemical vapor deposition to form a Group 4 metal element-containing film and particularly can be used to uniformly form a Group 4 metal element-containing film having a thickness of several nm to several tens of nm on a substrate having a trench (groove) in its surface or porous substrate. For example, in a substrate having a fine trench (groove) with an aspect ratio of about 1 or more and a width of about 1 μm or less in its surface, the Group 4 metal element-containing novel compounds have an excellent effect of uniformly forming a Group 4 metal element-containing film having a thickness of several nm to several tens of nm on the entire surface of the substrate including a surface of the fine trench (groove) including a surface of the deepest portion of the fine trench (groove) and an upper surface of the fine trench (groove). According to an exemplary embodiment of the present disclosure, a method of preparing a Group 4 metal element-containing film can be applied to manufacturing commercial semiconductor devices. Particularly, in order to manufacture a DRAM semiconductor device, it is necessary to form a high dielectric material to a thickness of several nm on a substrate having a trench with a width of much less than 100 nm or 50 nm and an aspect ratio of 10:1, 20:1, or 30:1, or a deeper and narrower trench. Particularly, it is necessary to form a high dielectric material having a uniform thickness even at a temperature of 280° C., 300° C., or more, and, thus, a precursor composition with which a film having a uniform thickness can be formed on a very narrow and deep trench by atomic layer deposition (ALD) even at a high temperature is needed and thus a Ti, Zr, or Hf compound having very high thermal stability is needed to be used as the precursor composition.

The Group 4 metal element-containing compounds according to an exemplary embodiment of the present disclosure can be used as a precursor used for ALD, CVD, and the like and thus can provide properties, e.g., improved thermal stability, high volatility and/or increased deposition rate, required for manufacturing next-generation devices such as semiconductors and therefore can be usefully utilized for forming a Group 4 metal element-containing film or thin film.

Further, the Group 4 metal element-containing compounds according to an exemplary embodiment of the present disclosure can be applied in various fields such as catalyst and the like.

BEST MODE FOR CARRYING OUT THE INVENTION

Figure 1:
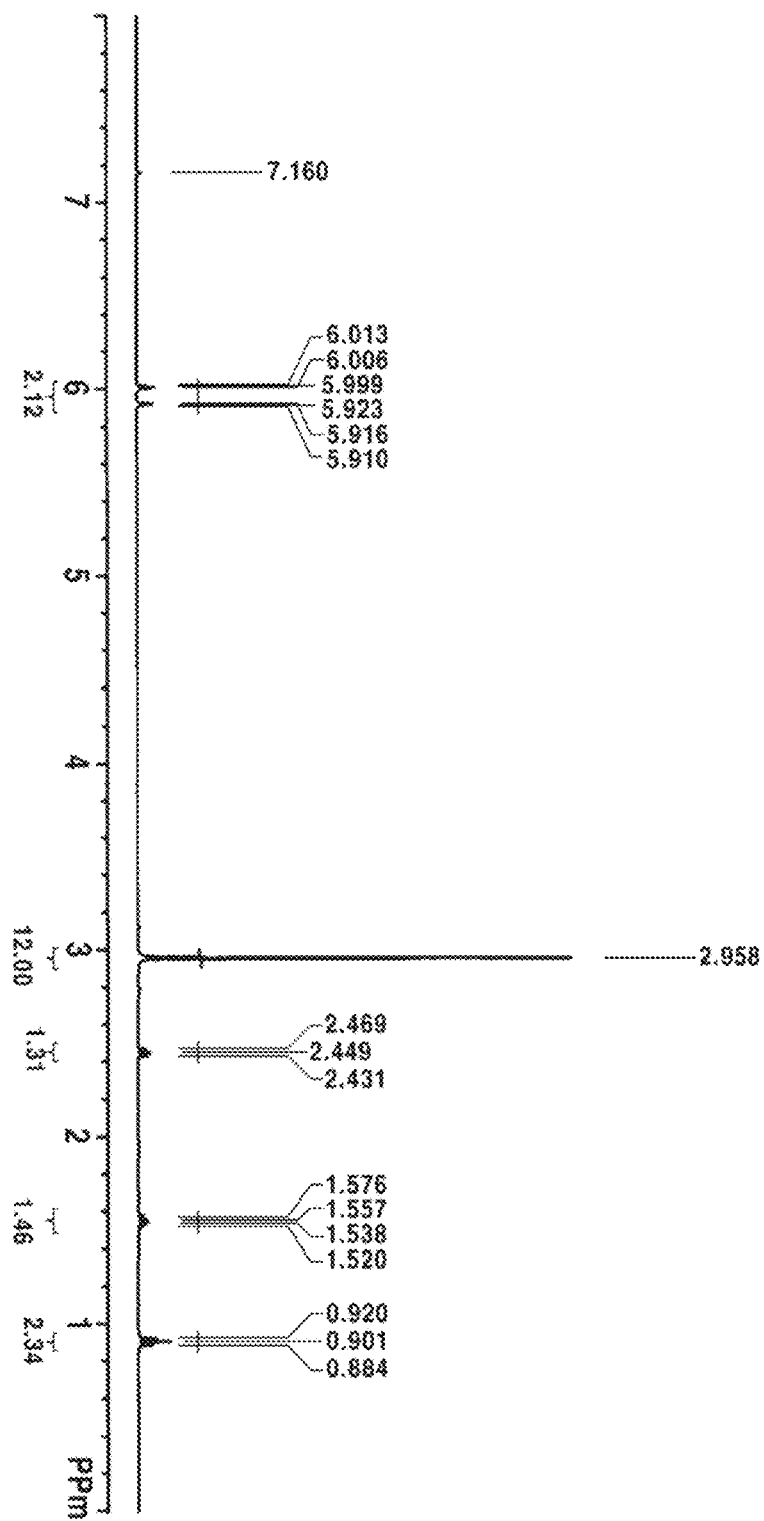
FIG. 1 is a H-HMR spectrum of a zirconium-containing compound prepared in accordance with an example of the present disclosure.

Hereinafter, examples of the present disclosure will be described in detail with reference to the accompanying drawings so that the present disclosure may be readily implemented by those skilled in the art. However, it is to be noted that the present disclosure is not limited to the examples but can be embodied in various other ways. In drawings, parts irrelevant to the description are omitted for the simplicity of explanation, and like reference numerals denote like parts through the whole document.

Through the whole document, the term "connected to" or "coupled to" that is used to designate a connection or coupling of one element to another element includes both a case that an element is "directly connected or coupled to" another element and a case that an element is "electronically connected or coupled to" another element via still another element.

Through the whole document, the term "on" that is used to designate a position of one element with respect to another element includes both a case that the one element is adjacent to the other element and a case that any other element exists between these two elements.

Further, through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "about or approximately" or "substantially" is intended to have meanings close to numerical values or ranges specified with an allowable error and intended to prevent accurate or absolute numerical values disclosed for understanding of the present disclosure from being illegally or unfairly used by any unconscionable third party.

Through the whole document, the term "step of" does not mean "step for".

Through the whole document, the term "combination(s) of" included in Markush type description means mixture or combination of one or more components, steps, operations and/or elements selected from a group consisting of components, steps, operation and/or elements described in Markush type and thereby means that the disclosure includes one or more components, steps, operations and/or elements selected from the Markush group.

Through the whole document, a phrase in the form "A and/or B" means "A or B, or A and B".

Through the whole document, the term "alkyl" includes linear or branched alkyl groups having 1 to 12 carbon atoms, 1 to 10 carbon atoms, 1 to 8 carbon atoms, 1 to 5 carbon atoms, or 1 to 4 carbon atoms and all the possible isomers thereof. For example, the alkyl group may include methyl group (Me), ethyl group (Et), n-propyl group ($^{n}$Pr), iso-propyl group ($^{i}$Pr), n-butyl group ($^{n}$Bu), tert-butyl group ($^{t}$Bu), iso-butyl group ($^{i}$Bu), sec-butyl group ($^{s}$Bu), pentyl group, hexyl group, iso-hexyl group, heptyl group, 4,4-dimethyl pentyl group, octyl group, 2,2,4-trimethyl pentyl group, nonyl group, decyl group, undecyl group, dodecyl group, and isomers thereof, but may not be limited thereto.

Through the whole document, the term "Group 4 metal element" refers to a chemical element belonging to the fourth group in the Periodic Table and may include Ti, Zr or Hf.

Through the whole document, the term "Cp" is the abbreviation of a "cyclopentadienyl" group.

Through the whole document, the term "Grignard reagent" refers to a reagent for mediating a Grignard reaction and may include alkyl, vinyl, or aryl-magnesium halide, but may not be limited thereto. The Grignard reaction refers to a metal organic chemical reaction in which the Grignard reagent is added to a carbonyl group of aldehyde or ketone.

Through the whole document, the term "halogen" or "halo" refers to fluorine (F), chlorine (Cl), bromine (Br), or iodine (I).

In the following description, exemplary embodiments of the present disclosure will be described in detail, but the present disclosure may not be limited thereto.

According to a first aspect of the present disclosure, there is provided a Group 4 metal element-containing compound, represented by the following Chemical Formula 1:

[Chemical Formula 1]

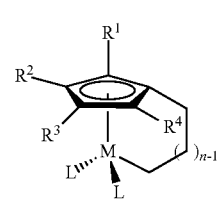

in the above Chemical Formula 1, M is Ti, Zr or Hf, L is $NR^5R^6$, $OR^7$ or a halogen, each of $R^1$ to $R^7$ is independently hydrogen or a linear or branched alkyl group having 1 to 4 carbon atoms, and n is an integer of from 1 to 3.

In an exemplary embodiment of the present disclosure, the Group 4 metal element-containing compound may be a compound represented by any one of the following Chemical Formulas 2 to 4, but may not be limited thereto:

[Chemical Formula 2]

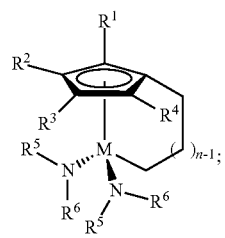

[Chemical Formula 3]

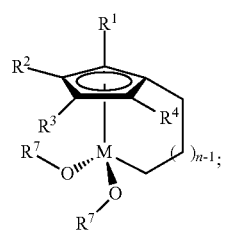

[Chemical Formula 4]

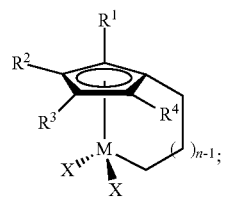

in the above Chemical Formulas, M is Ti, Zr or Hf, each of $R^1$ to $R^7$ is independently hydrogen or a linear or branched alkyl group having 1 to 4 carbon atoms, X is a halogen, and n is an integer of from 1 to 3.

In an exemplary embodiment of the present disclosure, in the above Chemical Formula 1, M may be Ti, Zr or Hf, L may be $N(CH_3)_2$, $N(C_2H_5)_2$, $N(CH_3)(C_2H_5)$, $OCH_3$, $OC_2H_5$, or Cl, and n may be from 1 to 3 or n may be 2, but may not be limited thereto.

In an exemplary embodiment of the present disclosure, the Group 4 metal element-containing compound represented by the above Chemical Formula 1 or any one of the above Chemical Formulas 2 to 4 may include compounds represented as the following structures, but may not be limited thereto:

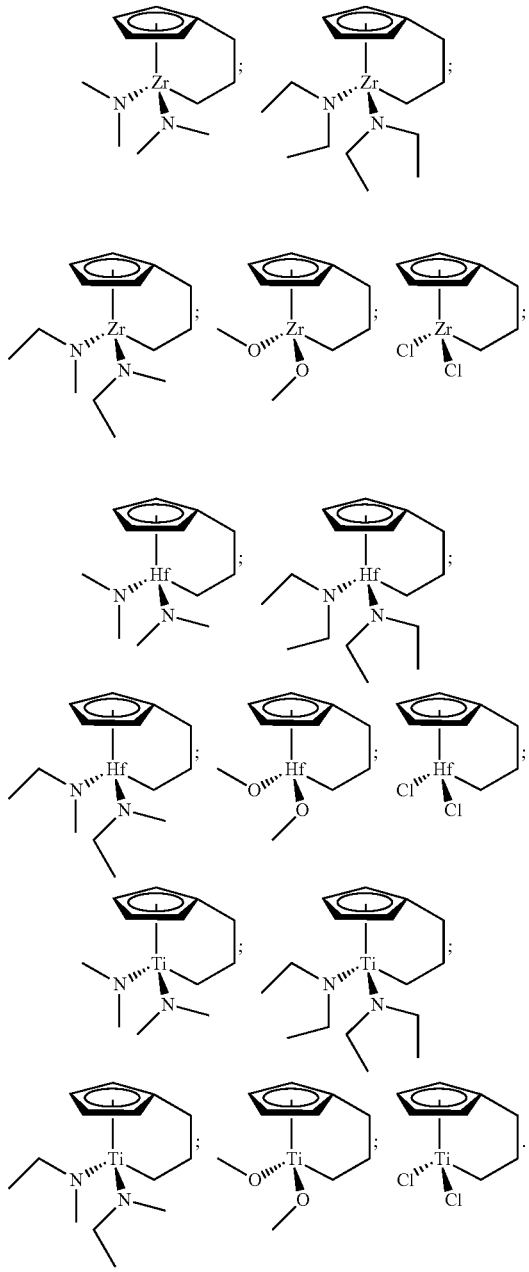

According to a second aspect of the present disclosure, there is provided a method of preparing a Group 4 metal element-containing compound represented by the following Chemical Formula 1, including reacting a compound represented by $ML_4$ with a Grignard reagent:

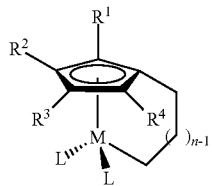

[Chemical Formula 1]

in the above Chemical Formula, M is Ti, Zr or Hf, L is $NR^5R^6$, $OR^7$ or a halogen, each of $R^1$ to $R^7$ is independently hydrogen or a linear or branched alkyl group having 1 to 4 carbon atoms, and n is an integer of from 1 to 3.

A Group 4 metal element-containing represented by the above Chemical Formula 1 refers to compounds described in the first aspect of the present disclosure and refers to, for example, compounds represented by any one of the above Chemical Formulas 2 to 4 as described in the first aspect of the present disclosure and specifically exemplified compounds therefor.

In an exemplary embodiment of the present disclosure, the Grignard reagent includes a material represented as $Cp(CH_2)_{n+1}MgX$, and in the above Chemical Formula, n may be an integer of from 1 to 3 and X may be a halogen, but may not be limited thereto.

In an exemplary embodiment of the present disclosure, the method of preparing a Group 4 metal element-containing compound may include a reaction as shown in the following Reaction Formula 1, but may not be limited thereto:

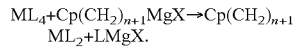

$ML_4 + Cp(CH_2)_{n+1}MgX \rightarrow Cp(CH_2)_{n+1}ML_2 + LMgX$. [Reaction Formula 1]

In the above Reaction Formula 1, M, L, and n are the same as defined with respect to the above Chemical Formula 1, and X is a halogen element selected from the group consisting of Cl, Br and I.

In an exemplary embodiment of the present disclosure, the $ML_4$ may be, e.g., tetrakis(dimethylamino)zirconium $[Zr(NMe_2)_4]$, tetrakis(diethylamino)zirconium $[Zr(NEt_2)_4]$, tetrakis(ethylmethylamino)zirconium $[Zr(NEtMe)_4]$, tetramethoxy zirconium $[Zr(OMe)_4]$, tetraethoxy zirconium $[Zr(OEt)_4]$, zirconium tetrachloride $(ZrCl_4)$, tetrakis(dimethylamino)hafnium $[Hf(NMe_2)_4]$, tetrakis(diethylamino) hafnium $[Hf(NEt_2)_4]$, tetrakis(ethylmethylamino)hafnium $[Hf(NEtMe)_4]$, tetramethoxy hafnium $[Hf(OMe)_4]$, tetraethoxy hafnium $[Hf(OEt)_4]$, hafnium tetrachloride $(HfCl_4)$, tetrakis(dimethylamino)titanium $[Ti(NMe_2)_4]$, tetrakis(diethylamino)titanium $[Ti(NEt_2)_4]$, tetrakis(ethylmethylamino)titanium $[Ti(NEtMe)_4]$, tetramethoxy titanium $[Ti(OMe)_4]$, tetraethoxy titanium $[Ti(OEt)_4]$, or titanium tetrachloride $(TiCl_4)$, but may not be limited thereto.

In an exemplary embodiment of the present disclosure, the Grignard reagent represented as $Cp(CH_2)_{n+1}MgX$ may be prepared by reacting $Cp(CH_2)_{n+1}X$ with magnesium (Mg) metal as shown in the following Reaction Formula 2, but may not be limited thereto:

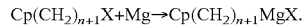

$Cp(CH_2)_{n+1}X + Mg \rightarrow Cp(CH_2)_{n+1}MgX$. [Reaction Formula 2]

According to a third aspect of the present disclosure, there is provided a method of preparing a Group 4 metal element-containing compound represented by the following Chemical Formula 1', including reacting a compound represented by the following Chemical Formula 4 with $M'NR^5R^6$ as an alkali metal salt of a dialkylamine or $M'OR^7$ as an alkali metal salt of an alcohol, and herein, M' is an alkali metal and each of R⁵ to R⁷ is independently hydrogen or a linear or branched alkyl group having 1 to 4 carbon atoms:

[Chemical Formula 4]

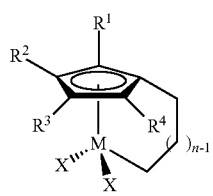

in the above Chemical Formula 4, M is Ti, Zr or Hf, each of R¹ to R⁴ is independently hydrogen or a linear or branched alkyl group having 1 to 4 carbon atoms, X is a halogen, and n is an integer of from 1 to 3;

[Chemical Formula 1']

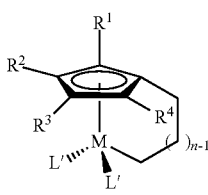

in the above Chemical Formula 1', M is Ti, Zr or Hf, L' is NR⁵R⁶ or OR⁷, each of R¹ to R⁷ is independently hydrogen or a linear or branched alkyl group having 1 to 4 carbon atoms, and n is an integer of from 1 to 3.

A Group 4 metal element-containing represented by the above Chemical Formula 1' refers to compounds represented by Chemical Formula 2 or 3 and specifically the exemplified compounds therefor among compounds represented by Chemical Formula 1 in the first aspect of the present disclosure.

In an exemplary embodiment of the present disclosure, the M'NR⁵R⁶ as an alkali metal salt of a dialkylamine may be, e.g., dimethylaminolithium (LiNMe₂), diethylaminolithium (LiNEt₂), ethylmethylaminolithium (LiNEtMe), dimethylaminosodium (NaNMe₂), diethylaminosodium (NaNEt₂), ethylmethylaminosodium (NaNEtMe), dimethylaminopotassium (KNMe₂), diethylaminopotassium (KNEt₂), or ethylmethylaminopotassium (KNEtMe), but may not be limited thereto.

In an exemplary embodiment of the present disclosure, the M'OR⁷ as an alkali metal salt of an alcohol may be, e.g., methoxylithium (LiOMe), ethoxylithium (LiOEt), isopropoxylithium (LiOⁱPr), methoxysodium (NaOMe), ethoxysodium (NaOEt), isopropoxysodium (NaOⁱPr), methoxypotassium (KOMe), ethoxypotassium (KOEt), or isopropoxypotassium (KOⁱPr), but may not be limited thereto.

According to a fourth aspect of the present disclosure, there is provided a precursor composition for depositing a film, including a Group 4 metal element-containing compound according to the first aspect of the present disclosure.

In an exemplary embodiment of the present disclosure, the precursor composition for depositing a film may be used for depositing a Group 4 metal element-containing film or thin film. The Group 4 metal element-containing film or thin film may have a thickness of from about 1 nm to several μm, but may not be limited thereto.

The Group 4 metal element-containing compound according to the first aspect of the present disclosure is represented by the following Chemical Formula 1:

[Chemical Formula 1]

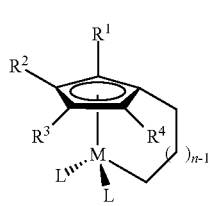

in the above Chemical Formula 1, M is Ti, Zr or Hf, L is NR⁵R⁶, OR⁷ or a halogen, each of R¹ to R⁷ is independently hydrogen or a linear or branched alkyl group having 1 to 4 carbon atoms, and n is an integer of from 1 to 3.

In an exemplary embodiment of the present disclosure, the Group 4 metal element-containing compound may be a compound represented by the following Chemical Formulas 2 to 4, but may not be limited thereto:

[Chemical Formula 2]

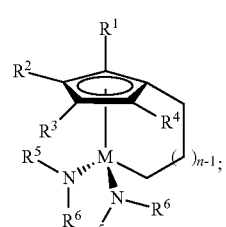

[Chemical Formula 3]

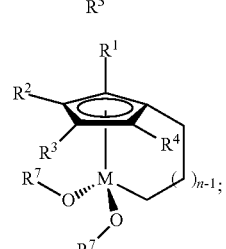

[Chemical Formula 4]

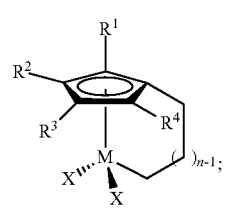

in the above Chemical Formulas, M is Ti, Zr or Hf, each of R¹ to R⁷ is independently hydrogen or a linear or branched alkyl group having 1 to 4 carbon atoms, X is a halogen, and n is an integer of from 1 to 3.

In an exemplary embodiment of the present disclosure, in the above Chemical Formula 1, M may be Ti, Zr or Hf, L may be N(CH₃)₂, N(C₂H₅)₂, N(CH₃)(C₂H₅), OCH₃, OC₂H₅ or Cl, and n may be from 1 to 3, or n may be 2, but may not be limited thereto.

In an exemplary embodiment of the present disclosure, the Group 4 metal element-containing compound represented by the above Chemical Formula 1 or any one of the above Chemical Formulas 2 to 4 may include compounds represented as the following structures, but may not be limited thereto:

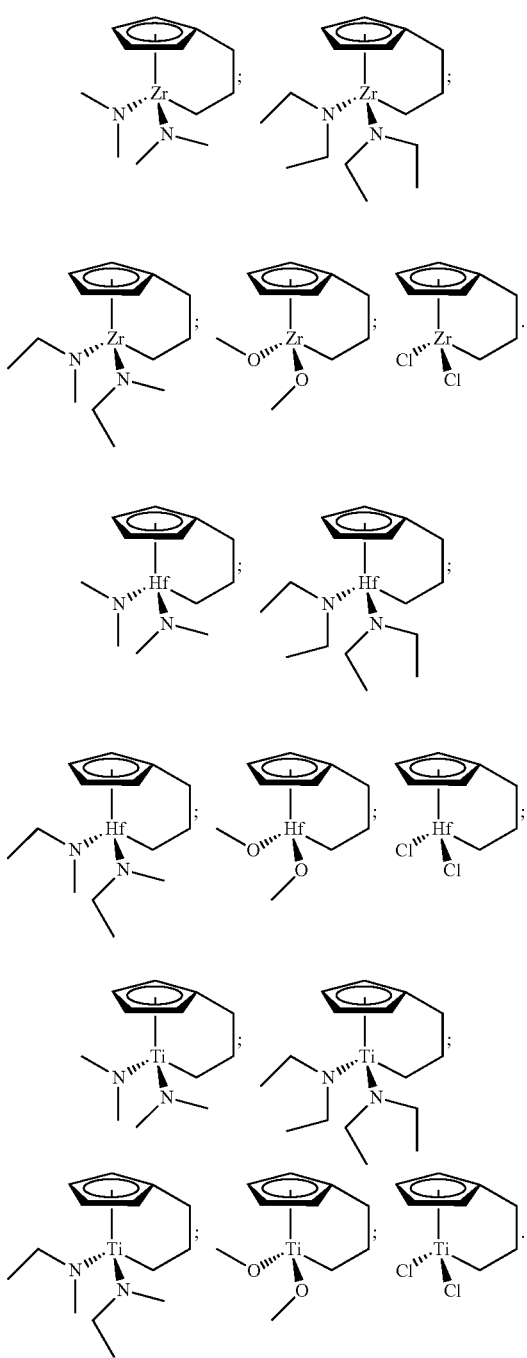

According to a fifth aspect of the present disclosure, there is provided a method of depositing a Group 4 metal element-containing film, including forming a Group 4 metal element-containing film using a precursor composition for depositing a film according to the fourth aspect of the present disclosure.

In an exemplary embodiment of the present disclosure, the Group 4 metal element-containing film or thin film may have a thickness of from about 1 nm to several μm, but may not be limited thereto.

In an exemplary embodiment of the present disclosure, the Group 4 metal element-containing film or thin film may be used as a high dielectric film in a semiconductor device, a catalyst, or the like, but may not be limited thereto.

In an exemplary embodiment of the present disclosure, a method of depositing a Group 4 metal element-containing film or thin film may include forming a Group 4 metal element-containing film or thin film by supplying and depositing the precursor composition to form a Group 4 metal element-containing film or thin film on a substrate positioned in a deposition chamber, but may not be limited thereto. The method of depositing a film may employ a method and an apparatus known in the art and may be performed using one or more additional reaction gases together if necessary. The substrate may employ a silicon semiconductor wafer and a compound semiconductor wafer, but may not be limited thereto. A substrate having a hole or trench may be used, and for example, a porous substrate having a large surface area may be used as a catalyst.

In an exemplary embodiment of the present disclosure, depositing the film may be performed by metal organic chemical vapor deposition (MOCVD) or atomic layer deposition (ALD), but may not be limited thereto. The metal organic chemical vapor deposition (MOCVD) or atomic layer deposition (ALD) may be performed using a deposition apparatus, deposition conditions, and additional reaction gases known in the art.

Specifically, according to the precursor composition for depositing a film according to the fourth aspect of the present disclosure and the method of depositing a Group 4 metal element-containing film or thin film according to the fifth aspect of the present disclosure including forming a Group 4 metal element-containing film or thin film using the precursor composition for depositing a film, the Group 4 metal element-containing novel compound according to an exemplary embodiment of the present disclosure which is included in the precursor composition for depositing a film has high thermal stability and thus can be used as a precursor for atomic layer deposition or chemical vapor deposition to form a Group 4 metal element-containing film and particularly can be used to uniformly form a Group 4 metal element-containing film having a thickness of several nm to several tens of nm on a substrate having a trench (groove) in its surface or porous substrate. For example, in a substrate having a fine trench (groove) with an aspect ratio of about 1 or more, 2 or more, 5 or more, 10 or more, 20 or more, 30 or more or 40 or more and a width of about 1 μm or less, 500 nm or less, 400 nm or less, 300 nm or less, 200 nm or less, 100 nm or less, 80 nm or less, 60 nm or less, 50 nm or less, 40 nm or less, 30 nm or less, 20 nm or less or 10 nm or less in its surface, the Group 4 metal element-containing novel compounds have an excellent effect of uniformly forming a Group 4 metal element-containing film having a thickness of from several nm to several tens of nm on the entire surface of the substrate including a surface of the fine trench (groove) including a surface of the deepest portion of the fine trench (groove) and an upper surface of the fine trench (groove).

The precursor composition for depositing a film according to the fourth aspect of the present disclosure and the method of depositing a Group 4 metal element-containing film or thin film according to the fifth aspect of the present disclosure including forming a Group 4 metal element-containing film or thin film using the precursor composition for depositing a film can be applied to manufacturing commercial semiconductor devices. Particularly, in order to manufacture a DRAM semiconductor device, it is necessary to form a high dielectric material to a thickness of several nm on a substrate having a groove with a width of much less than 100 nm or 50 nm and an aspect ratio of 10:1, 20:1, or 30:1, or a deeper and narrower groove. Particularly, it is necessary to form a high dielectric material having a uniform thickness even at a temperature of 280° C., 300° C., or more, and, thus, a precursor composition with which a film having a uniform thickness can be formed on a very narrow and deep groove by atomic layer deposition (ALD) even at a high temperature is needed and a Ti, Zr, or Hf compound having very high thermal stability is needed to be used as the precursor composition, and therefore, the precursor composition for depositing a film according to the fourth aspect of the present disclosure and the method of depositing a Group 4 metal element-containing film or thin film according to the fifth aspect of the present disclosure including forming a Group 4 metal element-containing film or thin film using the precursor composition for depositing a film can be usefully utilized.

MODE FOR CARRYING OUT THE INVENTION

Hereinafter, the present disclosure will be explained in more detail with reference to Examples. However, the following Examples are illustrative only for better understanding of the present disclosure but do not limit the present disclosure.

EXAMPLES

<Preparation Example 1> Preparation of Cp(CH$_2$)$_3$MgCl

After 11.2 g (0.462 mol, 3 equivalents) of magnesium and 100 mL of tetrahydrofuran (THF, C$_4$H$_8$O) were put into a flame-dried 1 L Schlenk flask, the flask was maintained at room temperature. After 21.8 g (0.154 mol, 1 equivalent) of 3-chloro-propylcyclopentadiene was added to the flask, the obtained reaction solution was stirred for 15 hours while the temperature was slowly increased to 50° C. Then, the temperature of the flask was slowly decreased to room temperature and the reaction solution was filtered through a celite pad and a glass frit to remove excess magnesium, and, thus Grignard reagent Cp(CH$_2$)$_3$MgCl was obtained from the obtained filtrate.

<Example 1> Preparation of Cp(CH$_2$)$_3$Zr[N(CH$_3$)$_2$]$_2$

After 41 g (0.154 mol, 1 equivalent) of tetrakis(dimethylamino)zirconium [Zr(N(CH$_3$)$_2$)$_4$] and 100 mL of n-hexane (C$_6$H$_{14}$) were put into a flame-dried 1 L Schlenk flask, the flask was maintained at room temperature. After the Grignard reagent Cp(CH$_2$)$_3$MgCl (0.154 mol, 1 equivalent) prepared in Preparation Example 1 was slowly drop-wisely added to the flask, the obtained reaction solution was refluxed for 15 hours.

After the reaction was completed, the solvent and volatile by-product were removed under a reduced pressure and extraction was carried out with 200 mL of n-hexane. After the n-hexane extract was filtered through a celite pad and a glass frit, the obtained filtrate was subject to a reduced pressure to remove the solvent and distilled under a reduced pressure, and, thus 27 g (yield of 61%) of pale yellow liquid compound Cp(CH$_2$)$_3$Zr[N(CH$_3$)$_2$]$_2$ which is a liquid zirconium compound represented as the following structure was obtained.

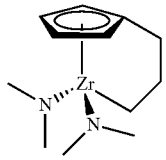

Boiling point (bp) 100° C. (0.3 torr);
Elemental analysis calcd for C$_{12}$H$_{22}$N$_2$Zr: C, 50.48, H, 7.77, N, 9.81; found C, 50.39, H, 7.81, N, 9.79.
1H-NMR (400 MHz, C$_6$D$_6$, 25° C.): δ 6.013, 5.923 (m, 4H, C$_5$H$_4$—CH$_2$CH$_2$CH$_2$), δ 2.958 (s, 12H, N(CH$_3$)$_2$), δ 2.469 (t, 2H, C$_5$H$_4$—CH$_2$CH$_2$CH$_2$), δ 1.576 (m, 2H, C$_5$H$_4$—CH$_2$CH$_2$CH$_2$), δ 0.920 (t, 2H, C$_5$H$_4$—CH$_2$CH$_2$CH$_2$).

A H-HMR spectrum of the zirconium-containing compound according to the present Example is as shown in FIG. 1. Further, a thermogravimetric analysis result for each of the zirconium-containing compound according to the present Example and CpZr[N(CH$_3$)$_2$]$_3$ according to Comparative Example is as shown in FIG. 2.

Figure 2:
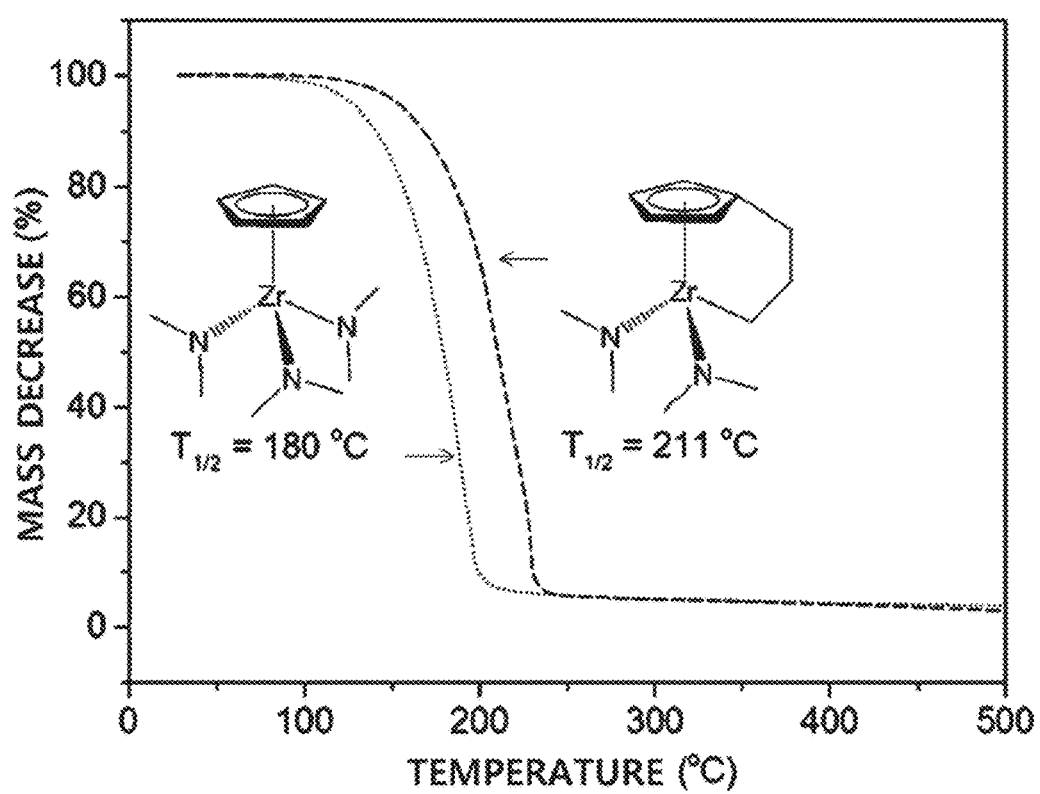
FIG. 2 is a thermogravimetric analysis graph for each of the zirconium-containing compound prepared in accordance with an example of the present disclosure and a compound according to a comparative example.

As can be seen from the thermogravimetric analysis result shown in FIG. 2, T$_{1/2}$ of the liquid zirconium compound according to the present Example was 211° C. and T$_{1/2}$ of the liquid zirconium compound according to Comparative Example was 180° C. Therefore, it can be confirmed that the liquid zirconium compound according to the present Example had a remarkably high T$_{1/2}$ as compared with the compound according to Comparative Example, and the residue amount was about 3% according to the thermogravimetric analysis, and, thus, it can be confirmed that the liquid zirconium compound according to the present Example had higher thermal stability and also had excellent thermal decomposition characteristics. These excellent characteristics demonstrate that the liquid zirconium compound according to the present Example is very advantageous to be used as a precursor for forming a film (thin film).

<Example 2> Preparation of Cp(CH$_2$)$_3$Zr[N(C$_2$H$_5$)$_2$]$_2$ and Cp(CH$_2$)$_3$Zr[N(CH$_3$)C$_2$H$_5$)]$_2$ A precursor material Cp(CH$_2$)$_3$Zr[N(C$_2$H$_5$)$_2$]$_2$ or Cp(CH$_2$)$_3$Zr[N(CH$_3$)(C$_2$H$_5$)]$_2$ was prepared by the same method as in Example 1 except that tetrakis(diethylamino)zirconium [Zr(N(C$_2$H$_5$)$_2$)$_4$] or tetrakis(ethylmethylamino)zirconium [Zr(N(CH$_3$)(C$_2$H$_5$))$_4$] was used instead of tetrakis(dimethylamino)zirconium [Zr(N(CH$_3$)$_2$)$_4$] used in Example 1.

<Example 3> Preparation of Cp(CH$_2$)$_3$Hf[N(CH$_3$)$_2$]$_2$

After 198 g (0.558 mol, 1 equivalent) of tetrakis(dimethylamino)hafnium [Hf(N(CH$_3$)$_2$)$_4$] and 500 mL of n-hexane were put into a flame-dried 1 L Schlenk flask, the flask was maintained at room temperature. After the Grignard reagent Cp(CH$_2$)$_3$MgCl (0.558 mol, 1 equivalent) prepared in Preparation Example 1 was slowly drop-wisely added to the flask, the obtained reaction solution was refluxed for 15 hours.

Figure 3:
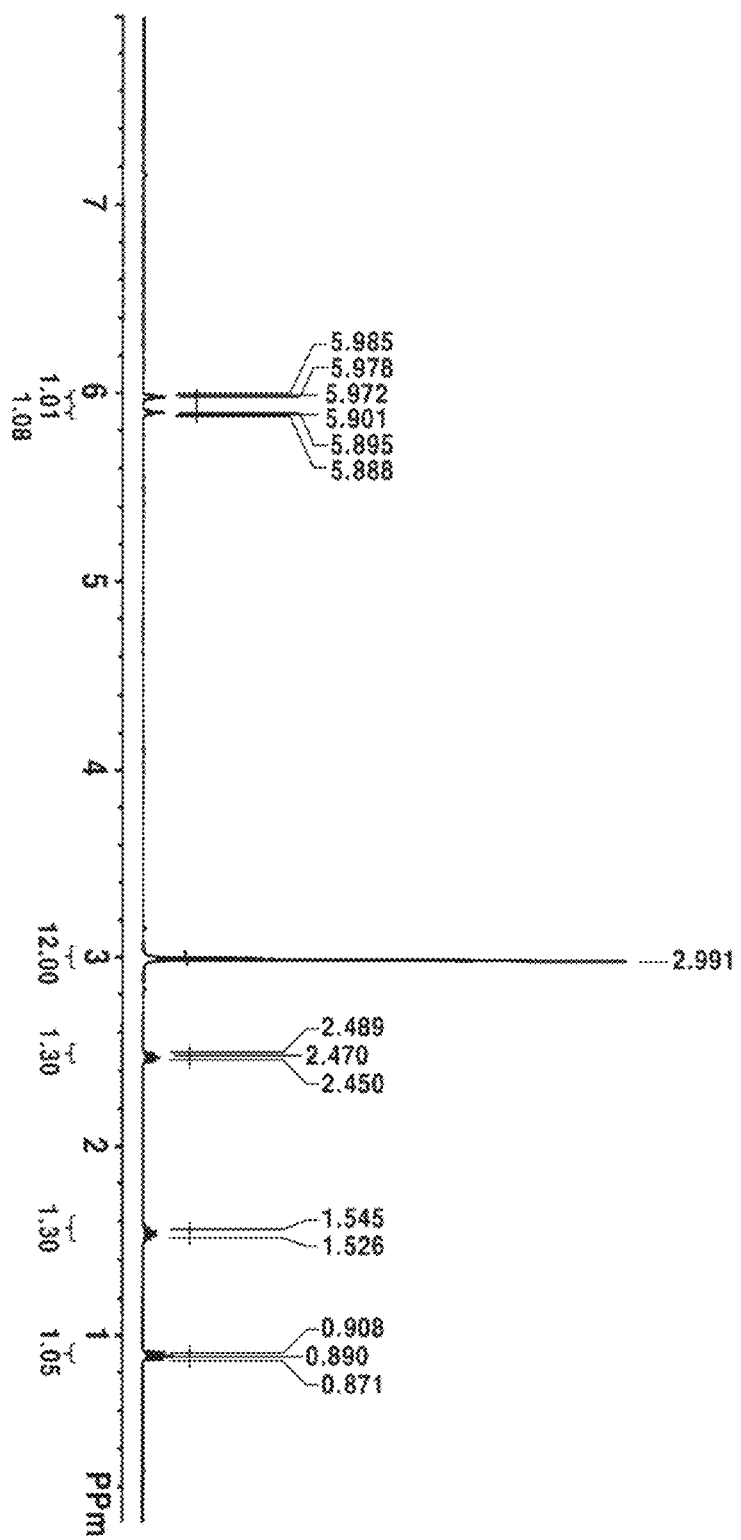
FIG. 3 is a H-HMR spectrum of a hafnium-containing compound prepared in accordance with an example of the present disclosure.

After the reaction was completed, the solvent and volatile by-product were removed under a reduced pressure and extraction was carried out with 1000 mL of n-hexane. After the n-hexane extract was filtered through a celite pad and a glass frit, the obtained filtrate was subject to a reduced pressure to remove the solvent and distilled under a reduced pressure, and, thus, 108 g (yield of 52%) of pale yellow liquid compound $Cp(CH_2)_3Hf[N(CH_3)_2]_2$ represented as the following structure was obtained. A H-HMR spectrum of the liquid hafnium compound obtained as above is shown in FIG. 3.

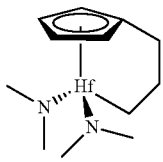

Boiling point (bp) 100° C. (0.3 torr);
Elemental analysis calcd for $C_{12}H_{21}N_2Hf$: C, 38.66, H, 5.95, N, 7.51; found C, 38.56, H, 5.99, N, 7.49.
1H-NMR (400 MHz, $C_6D_6$, 25° C.): δ 5.985, 5.901 (m, 4H, $C_5\underline{H}_4$—$CH_2CH_2CH_2$), δ 2.991 (s, 12H, $N(C\underline{H}_3)_2$), δ 2.489 (t, 2H, $C_5H_4$—$CH_2CH_2C\underline{H}_2$), δ 1.545 (m, 2H, $C_5H_4$—$C\underline{H}_2CH_2CH_2$), δ 0.908 (t, 2H, $C_5H_4$—$CH_2C\underline{H}_2CH_2$)

<Example 4> Preparation of $Cp(CH_2)_3Hf[N(C_2H_5)_2]_2$ and $Cp(CH_2)_3Hf[N(CH_3)(C_2H_5)]_2$ The precursor $Cp(CH_2)_3Hf[N(C_2H_5)_2]_2$ or $Cp(CH_2)_3Hf[N(CH_3)(C_2H_5)]_2$ was prepared by the same method as in Example 3 except that tetrakis(diethylamino)hafnium $[Hf(N(C_2H_5)_2)_4]$ or tetrakis(ethylmethylamino)hafnium $[Hf(N(CH_3)(C_2H_5))_4]$ was used instead of tetrakis(dimethylamino)hafnium $[Hf(N(CH_3)_2)_4]$ used in Example 3.

<Example 5> Preparation of $Cp(CH_2)_3TiCl_2$

Figure 4:
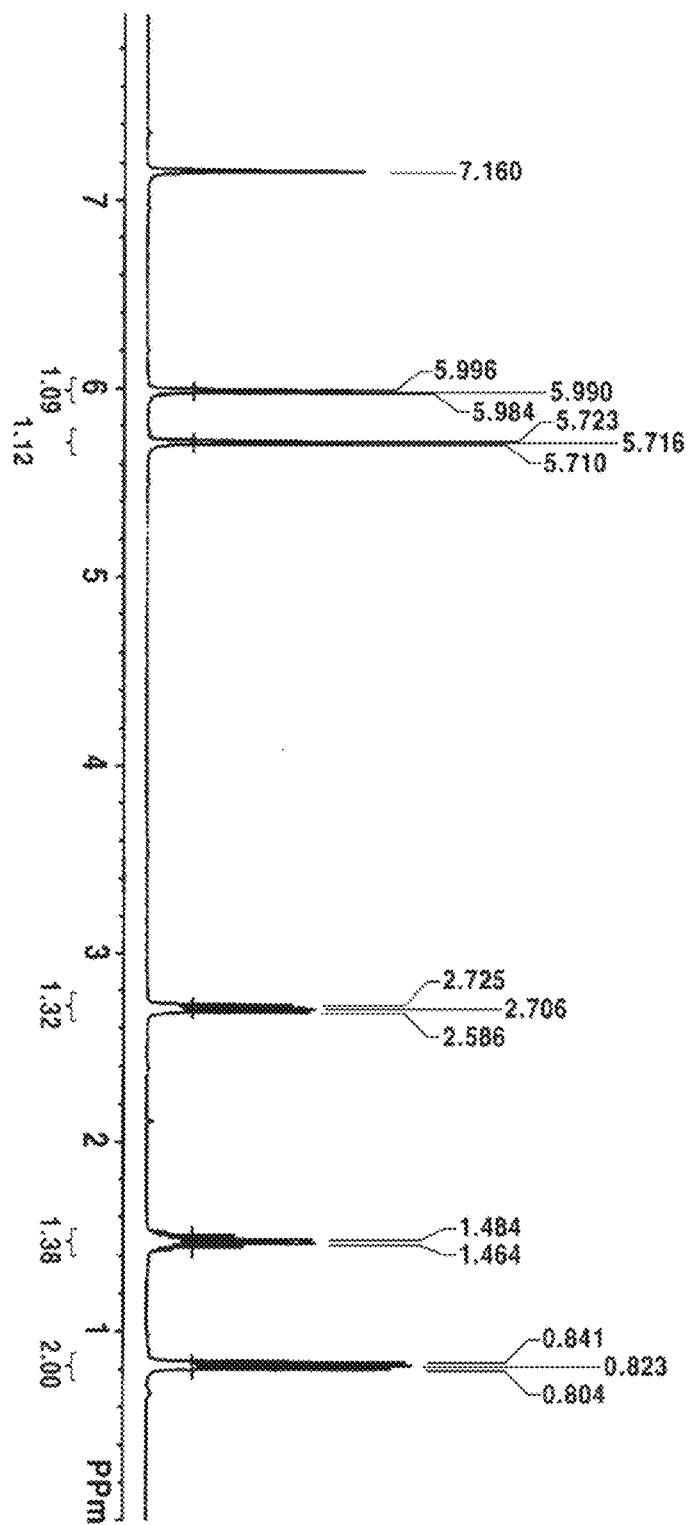
FIG. 4 is a H-HMR spectrum of a titanium-containing compound prepared in accordance with an example of the present disclosure.

After 99 g (0.522 mol, 1 equivalent) of titanium tetrachloride ($TiCl_4$) and 1000 mL of toluene ($C_6H_5$—$CH_3$) were put into a flame-dried 3 L Schlenk flask, the flask was cooled at −10° C. After the Grignard reagent $Cp(CH_2)_3MgCl$ (0.522 mol, 1 equivalent) prepared in Preparation Example 1 and 53 g (0.522 mol, 1 equivalent) of triethylamine were diluted in 500 mL of toluene and slowly drop-wisely added to the flask. The obtained reaction solution was refluxed for 15 hours.
After the reaction was completed, the solvent and volatile by-product were removed under a reduced pressure and washing was carried out with 200 mL of n-hexane three times and the reaction product was subject to a reduced pressure to remove the solvent and distilled under a reduced pressure, and, thus, 69 g (yield of 59%) of red solid compound $Cp(CH_2)_3TiCl_2$ represented as the following structure was obtained. A H-HMR spectrum of the above-described solid compound is as shown in FIG. 4:

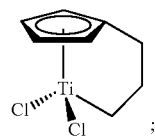

Elemental analysis calcd for $C_{12}H_{22}N_2Ti$: C, 42.72, H, 4.48; found C, 42.73, H, 4.46.
1H-NMR (400 MHz, $C_6D_6$, 25° C.): δ 5.996, 5.723 (m, 4H, $C_5\underline{H}_4$—$CH_2CH_2CH_2$), δ 2.725 (t, 2H, $C_5H_4$—$CH_2CH_2C\underline{H}_2$), δ 1.484 (t, 2H, $C_5H_4$—$CH_2C\underline{H}_2CH_2$), δ 0.841 (m, 2H, $C_5H_4$—$C\underline{H}_2CH_2CH_2$)

<Example 6> Preparation of $Cp(CH_2)_3ZrCl_2$ and $Cp(CH_2)HfCl_2$

The precursor $Cp(CH_2)_3ZrCl_2$ or $Cp(CH_2)_3HfCl_2$ was prepared by the same method as in Example 5 except that zirconium tetrachloride ($ZrCl_4$) or hafnium tetrachloride ($HfCl_4$) was used instead of titanium tetrachloride ($TiCl_4$) used in Example 5.

<Example 7> Preparation of $Cp(CH_2)_3Ti[N(CH_3)_2]_2$

Figure 5:
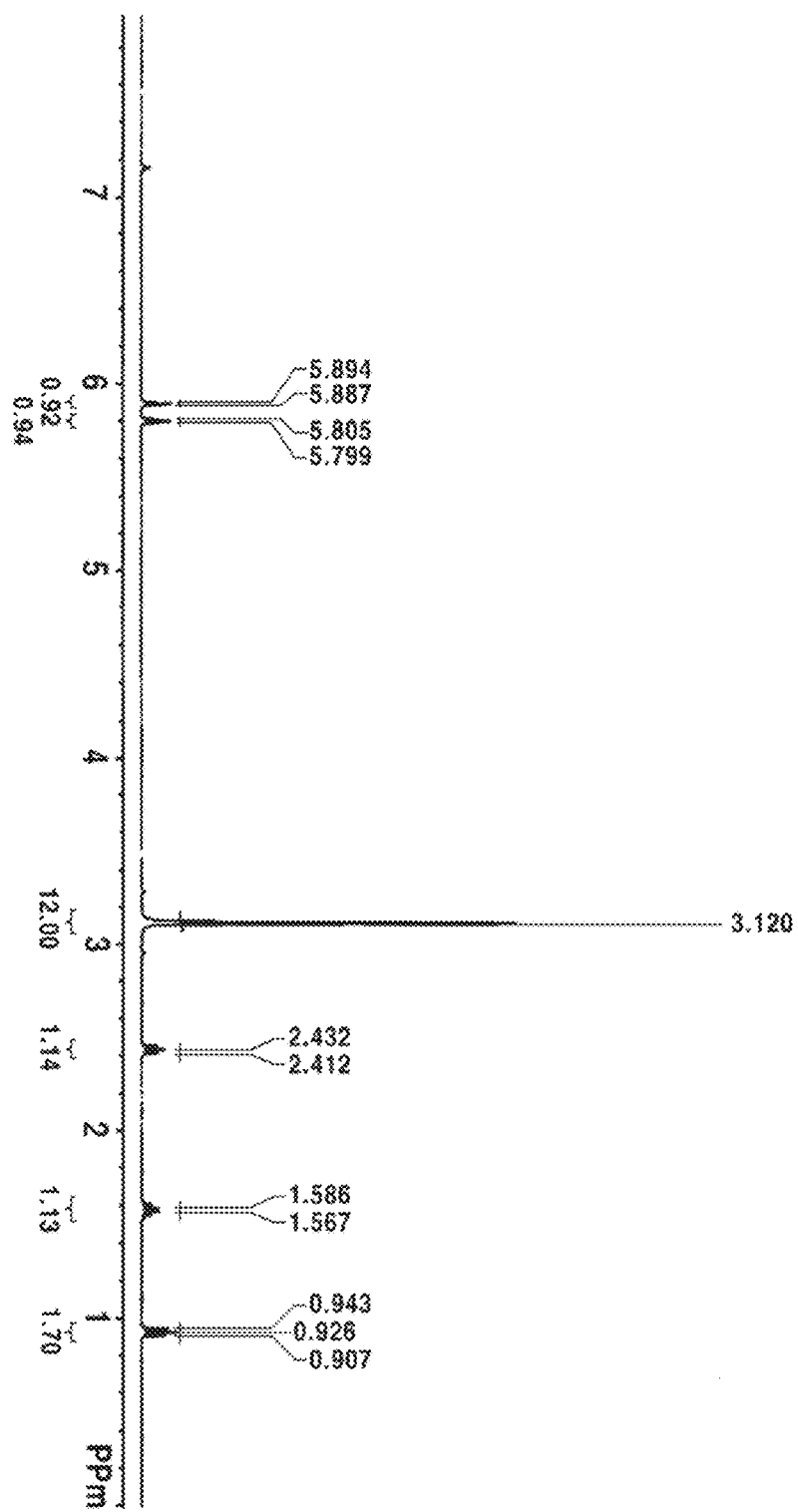
FIG. 5 is a H-HMR spectrum of a titanium-containing compound prepared in accordance with an example of the present disclosure.

After 277 g (1.044 mol, 2 equivalents) of n-butyllithium was put into a flame-dried 3 L Schlenk flask, the flask was cooled at −40° C. 47 g (1.044 mol, 2 equivalents) of dimethylamine was slowly drop-wisely added to the flask and then stirred at room temperature for 3 hours. After $Cp(CH_2)_3TiCl_2$ (0.522 mol, 1 equivalent) prepared in Example 3 was slowly drop-wisely added to the flask, the obtained reaction solution was stirred at 40° C. for 4 hours.
After the reaction was completed, the solvent and volatile by-product were removed under a reduced pressure and then extraction was carried out with 500 ml of n-hexane. After the n-hexane extract was filtered through a celite pad and a glass frit, the obtained filtrate subject to a reduced pressure to remove the solvent and distilled under a reduced pressure, and thus 50 g (yield of 40%) of red liquid compound $Cp(CH_2)_3Ti[N(CH_3)_2]_2$ represented as the following structure was obtained. A H-HMR spectrum of the liquid compound prepared as above is as shown in FIG. 5:

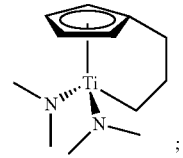

Boiling point (bp) 100° C. (0.3 torr);
Elemental analysis calcd for $C_{12}H_{22}N_2Ti$: C, 59.51, H, 9.16, N, 11.57; found C, 59.48, H, 9.17, N, 11.58.
1H-NMR (400 MHz, $C_6D_6$, 25° C.): δ 5.894, 5.805 (m, 4H, $C_5\underline{H}_4$—$CH_2CH_2C\underline{H}_2$), δ 3.120 (s, 12H, $N(C\underline{H}_3)_2$), δ 2.432 (t, 2H, $C_5H_4$—$CH_2CH_2C\underline{H}_2$), δ 1.586 (m, 2H, $C_5H_4$—$CH_2C\underline{H}_2CH_2$), δ 0.943 (t, 2H, $C_5H_4$—$C\underline{H}_2CH_2CH_2$)

<Example 8> Preparation of $Cp(CH_2)_3Ti(OCH_3)_2$, $Cp(CH_2)_3Zr(OCH_3)_2$ and $Cp(CH_2)_3Hf(OCH_3)_2$ The precursor $Cp(CH_2)_3Ti(OCH_3)_2$ was prepared by the same method as in Example 7 except that methanol was used instead of dimethylamine used in Example 7.
Further, the precursor material $Cp(CH_2)_3Zr(OCH_3)_2$ or $Cp(CH_2)_3Hf(OCH_3)_2$ was prepared by the same method as in Example 7 except that $Cp(CH_2)_3ZrCl_2$ or $Cp(CH_2)_3HfCl_2$ was used instead of $Cp(CH_2)_3TiCl_2$ used in Example 7 and methanol was used instead of dimethylamine.

<Example 9> Formation of Zirconium Oxide Film by Atomic Layer Deposition Using $Cp(CH_2)_3Zr[N(CH_3)_2]_2$ Compound and Ozone ($O_3$) Gas A test for forming a zirconium oxide film by atomic layer deposition (ALD) using $Cp(CH_2)_3Zr[N(CH_3)_2]_2$ prepared in Example 1 as a precursor was conducted. In this case, a silicon (Si) wafer having a fine groove (trench) with a width of about 55 nm and an aspect ratio of about 10:1 was used as a substrate. The substrate was heated at 290° C. to 350°

Figure 6:
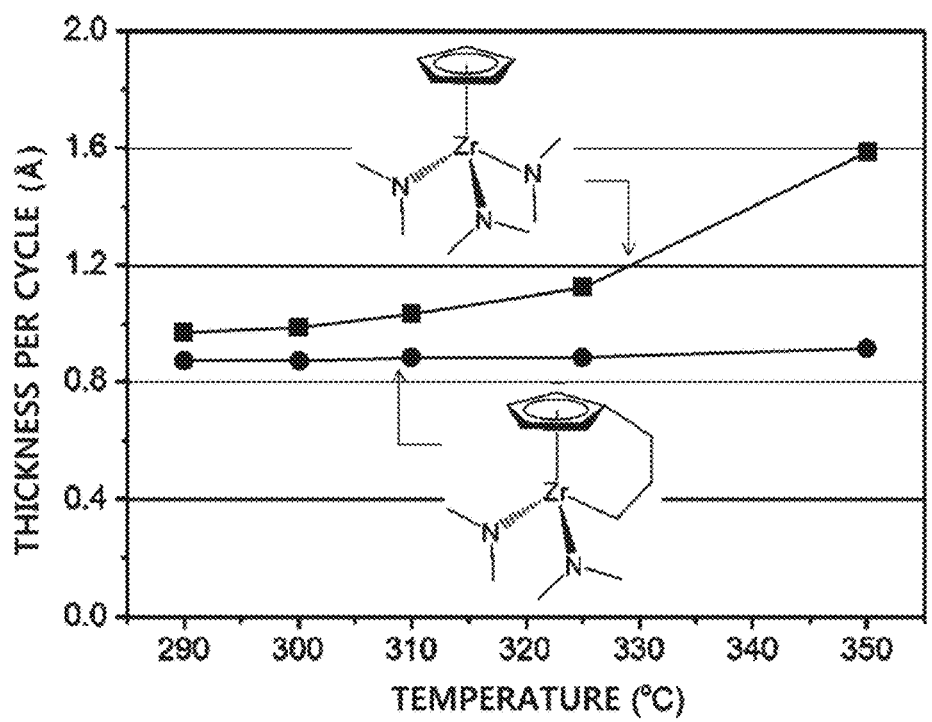
FIG. 6 shows film growth by atomic layer deposition using the zirconium-containing compound prepared in accordance with an example of the present disclosure and film growth according to a comparative example, depending on a substrate temperature.

C. Further, a precursor compound put in a stainless-steel container was heated at a temperature of 100° C., and the precursor compound was supplied to an ALD reactor for performing atomic layer deposition by allowing argon (Ar) gas to pass through the container at a flow rate of 60 sccm. An internal pressure in the ALD reactor was maintained at 3 torr. An ALD source supply cycle, in which a gas of the precursor compound was supplied to the ALD reactor for 5 seconds, then, argon gas was supplied for 5 seconds, and then, ozone (O$_3$) gas was supplied for 5 seconds and argon gas was supplied again for 5 seconds, was repeated 200 times. Film growth per source supply cycle of the zirconium oxide thin film formed according to the above-described process was as shown in FIG. 6. As shown in FIG. 6, it was observed that film growth per ALD source supply cycle was uniform in the range of the substrate temperature of from 290° C. to 350° C.

Figure 7:
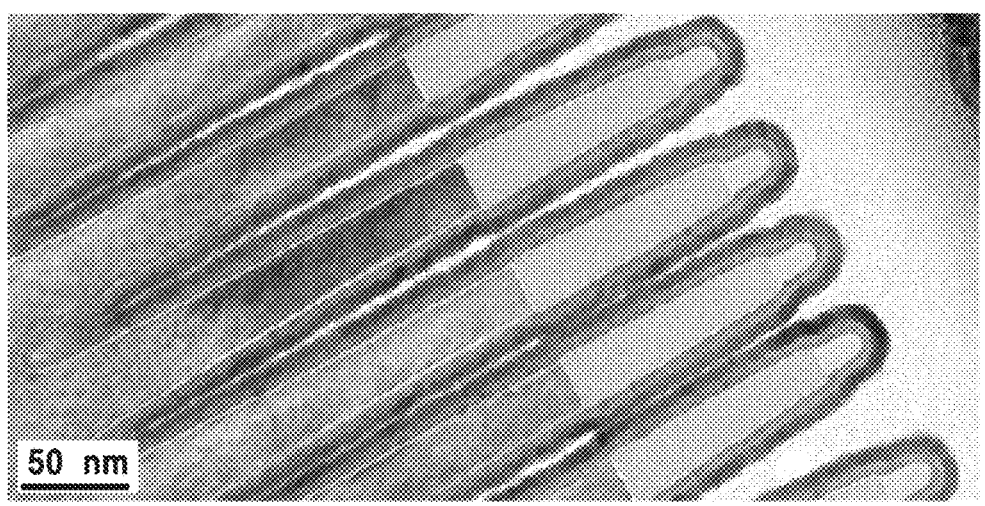
FIG. 7 shows a transmission electron microscope (TEM) observation result of a cross section of a film formed using the zirconium-containing compound prepared in accordance with an example of the present disclosure on a substrate including a narrow trench.

FIG. 7 shows a transmission electron microscope (TEM) observation result of a cross section of a film formed by heating a substrate including a very narrow trench (groove) with an aspect ratio of 10:1 at 300° C. and repeating the above-described ALD source supply cycle 80 times. It can be confirmed that a film having a uniform thickness of about 7 nm was formed on the entire surface of the substrate including a surface of the deepest portion of the trench in the substrate and an upper surface of the trench.

<Comparative Example 1> Formation of Zirconium Oxide Film by Atomic Layer Deposition Using CpZr[N(CH$_3$)$_2$]$_3$ Compound and Ozone (O$_3$) Gas A zirconium oxide film was formed under the same conditions as in Example 9 except that CpZr[N(CH$_3$)$_2$]$_3$ was used instead of Cp(CH$_2$)$_3$Zr[N(CH$_3$)$_2$]$_2$ and CpZr[N(CH$_3$)$_2$]$_3$ put in a stainless-steel container was heated at a temperature of 90° C. Film growth per ALD source supply cycle of the zirconium oxide thin film formed according to the above-described process was as shown in FIG. 6. It was observed that when a temperature of the silicon (Si) substrate was 300° C. or more, film growth per source supply cycle was increased as the temperature was increased. Particularly, when the temperature of the substrate was 350° C., film growth per ALD source supply cycle was increased almost 2 times compared with film growth at 290° C. and 300° C. This was due to thermal decomposition of CpZr[N(CH$_3$)$_2$], and if the thermal decomposition is carried out as such, a zirconium oxide film having a uniform thickness cannot be formed on a substrate having a trench with a high aspect ratio by atomic layer deposition.

It can be seen from Example 9 and Comparative Example 1 that atomic layer deposition using a Zr compound of the present disclosure is more advantageous in forming a zirconium oxide film to a uniform thickness on the entire surface of a substrate having a trench (groove) and including a surface of the deepest portion of the trench and an upper surface of the trench at a higher temperature than atomic layer deposition using a CpZr[N(CH$_3$)$_2$]$_3$ gas and ozone gas conventionally known in the art.

Figure 8:
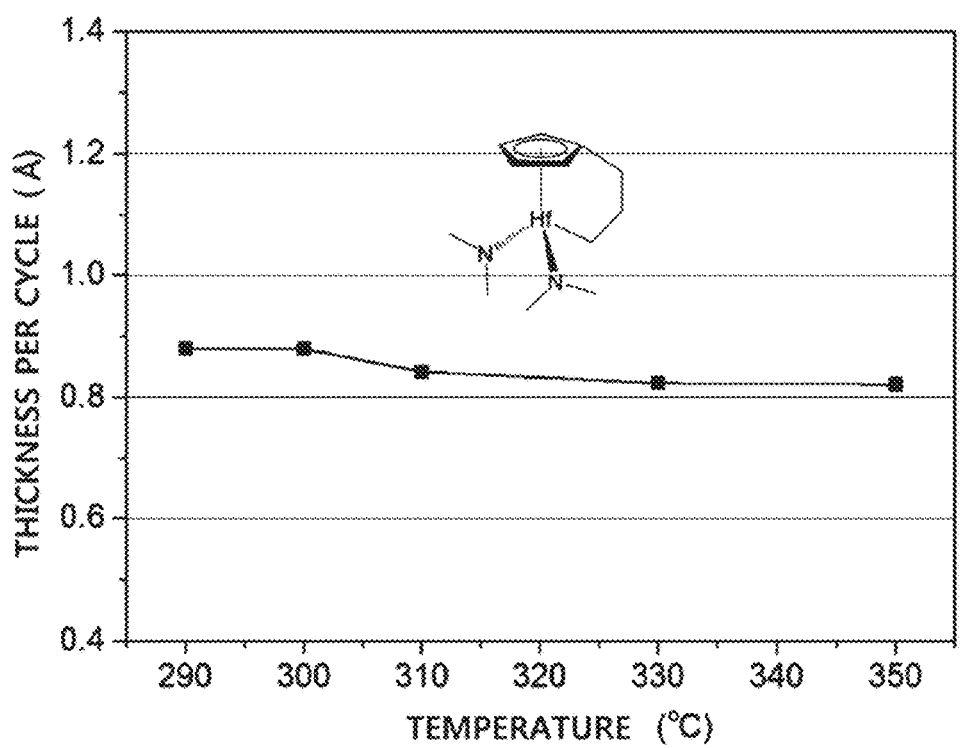
FIG. 8 shows film growth by atomic layer deposition using the hafnium-containing compound prepared in accordance with an example of the present disclosure, depending on a substrate temperature.

<Example 10> Formation of Hafnium Oxide Film by Atomic Layer Deposition Using Cp(CH$_2$)$_3$Hf[N(CH$_3$)$_2$]$_2$ Compound and Ozone (O$_3$) Gas A test for forming a hafnium oxide film by atomic layer deposition (ALD) using Cp(CH$_2$)$_3$Hf[N(CH$_3$)$_2$]$_2$ prepared in Example 3 as a precursor was conducted. In this case, a silicon (SI) wafer having a fine trench with a width of about 55 nm and an aspect ratio of about 10:1 was used as a substrate. The substrate was heated at 290° C. to 350° C. Further, a precursor compound put in a stainless-steel container was heated at a temperature of 100° C., and the precursor compound was supplied to an ALD reactor for performing atomic layer deposition by allowing argon (Ar) gas to pass through the container at a flow rate of 60 sccm. An internal pressure in the ALD reactor was maintained at 3 torr. An ALD source supply cycle, in which a gas of the precursor compound was supplied to the ALD reactor for 5 seconds, then, argon gas was supplied for 5 seconds, and then, ozone (O$_3$) gas was supplied for 5 seconds and argon gas was supplied again for 5 seconds, was repeated 200 times. Film growth per source supply cycle of the hafnium oxide thin film formed according to the above-described process is shown in FIG. 8. As shown in FIG. 8, it was observed that film growth per ALD source supply cycle was uniform in the range of substrate temperature of from 290° C. to 350° C.

Figure 9:
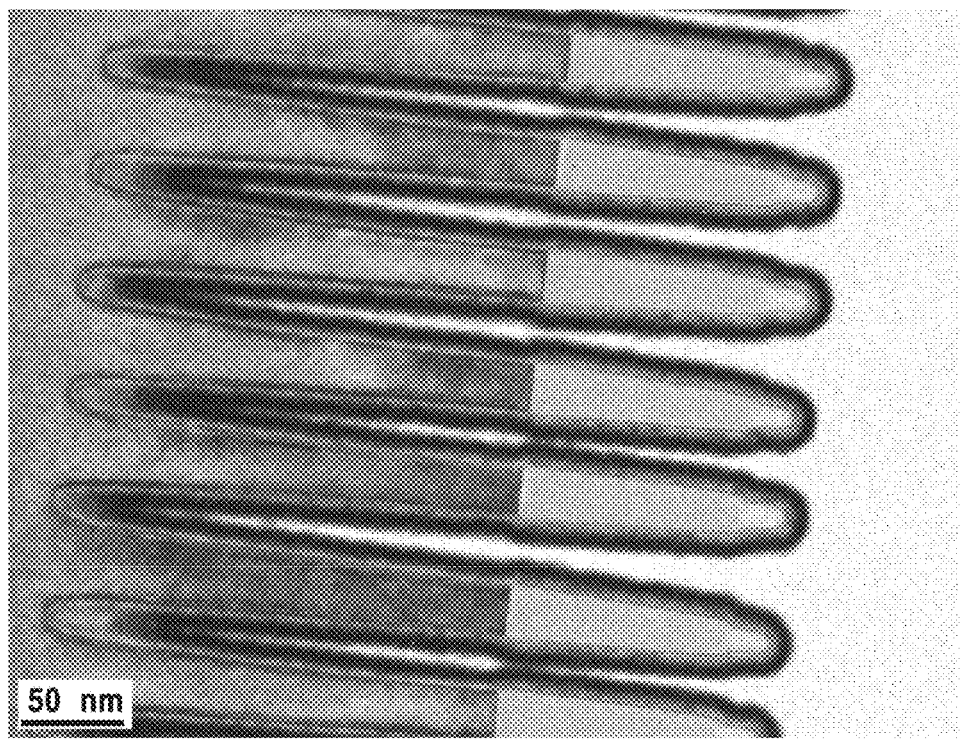
FIG. 9 shows a transmission electron microscope (TEM) observation result of a cross section of a film formed using the hafnium-containing compound prepared in accordance with an example of the present disclosure on a substrate including a narrow trench.

FIG. 9 shows a transmission electron microscope (TEM) observation result of a cross section of a film formed by heating a substrate including fine trenches with a width of about 55 nm and an aspect ratio of about 10:1 at 300° C. and repeating 61 times of the above-described ALD source supply cycle. It can be seen that a film having a uniform thickness of about 5 nm was formed on the entire surface of the substrate including a surface of the deepest portion of the trench and an upper surface of the trench in the substrate.

The above description of the present disclosure is provided for the purpose of illustration, and it would be understood by those skilled in the art that various changes and modifications may be made without changing technical conception and essential features of the present disclosure. Thus, it is clear that the above-described examples are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

We claim:

1. A Group 4 metal element-containing compound, represented by the following Chemical Formula 1:

[Chemical Formula 1]

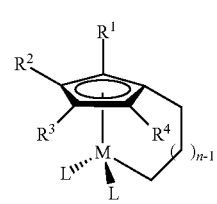

in the above Chemical Formula 1,
M is Ti, Zr or Hf,
L is NR$^5$R$^6$ or a halogen,
each of R$^1$ to R$^4$ is independently hydrogen or a linear or branched alkyl group having 1 to 4 carbon atoms,
each of R$^5$ and R$^6$ is independently a linear or branched alkyl group having 1 to 4 carbon atoms, and
n is an integer of from 1 to 3.

2. The compound of claim 1,
wherein the Group 4 metal element-containing compound is represented by the following Chemical Formula 2:

[Chemical Formula 2]

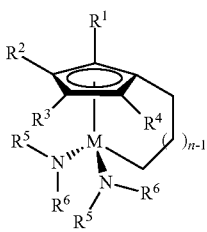

in the above Chemical Formula 2,
M is Ti, Zr or Hf,
each of $R^1$ to $R^4$ is independently hydrogen or a linear or branched alkyl group having 1 to 4 carbon atoms,
each of $R^5$ and $R^6$ is independently a linear or branched alkyl group having 1 to 4 carbon atoms, and
n is an integer of from 1 to 3.

3. The compound of claim 1,
wherein the Group 4 metal element-containing compound is represented by the following Chemical Formula 4:

[Chemical Formula 4]

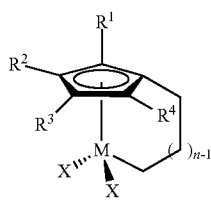

in the above Chemical Formula 4,
M is Ti, Zr or Hf,
each of $R^1$ to $R^4$ is independently hydrogen or a linear or branched alkyl group having 1 to 4 carbon atoms,
X is a halogen, and
n is an integer of from 1 to 3.

4. The compound of claim 1,
wherein M is Ti, Zr or Hf, L is $N(CH_3)_2$, $N(C_2H_5)_2$, $N(CH_3)(C_2H_5)$ or Cl, and n is an integer of from 1 to 3.

5. A method of preparing a Group 4 metal element-containing compound represented by the following Chemical Formula 1, comprising reacting a compound represented by ML with a Grignard reagent:

[Chemical Formula 1]

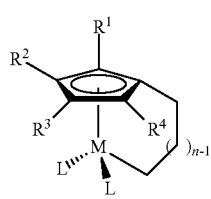

in the above Chemical Formula,
M is Ti, Zr or Hf,
L is $NR^5R^6$ or a halogen,
each of $R^1$ to $R^4$ is independently hydrogen or a linear or branched alkyl group having 1 to 4 carbon atoms,
each of $R^5$ and $R^6$ is independently a linear or branched alkyl group having 1 to 4 carbon atoms, and
n is an integer of from 1 to 3.

6. The method of claim 5,
wherein the Grignard reagent includes a material represented as Chemical Formula $Cp(CH_2)_{n+1}MgX$, and
in the above Chemical Formula,
$Cp(CH_2)_{n+1}$ represents

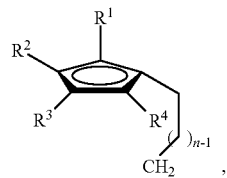

each of $R^1$ to $R^4$ is independently hydrogen or a linear or branched alkyl group having 1 to 4 carbon atoms,
n is an integer of from 1 to 3, and
X is a halogen.

7. The method of claim 6,
wherein the material represented as $Cp(CH_2)_{n+1}MgX$ is prepared by reacting $Cp(CH_2)_{n+1}X$ with Mg, and
in the $Cp(CH_2)_{n+1}X$,
$Cp(CH_2)_{n+1}$ represents

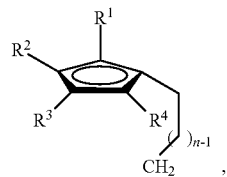

each of $R^1$ to $R^4$ is independently hydrogen or a linear or branched alkyl group having 1 to 4 carbon atoms,
n is an integer of from 1 to 3, and
X is a halogen.

8. A precursor composition for depositing a film, comprising a Group 4 metal element-containing compound of claim 1.

9. A method of depositing a Group 4 metal element-containing film, comprising forming a Group 4 metal element-containing film using a precursor composition for depositing a film of claim 8.

10. A method of preparing a Group 4 metal element-containing compound represented by the following Chemical Formula 1', comprising reacting a compound represented by the following Chemical Formula 4 with $M'NR^5R^6$ as an alkali metal salt of a dialkylamine, wherein M' is an alkali metal and each of $R^5$ and $R^6$ is independently a linear or branched alkyl group having 1 to 4 carbon atoms:

[Chemical Formula 4]

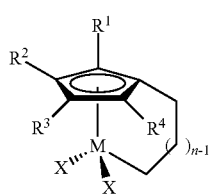

in the above Chemical Formula 4,
M is Ti, Zr or Hf,
each of $R^1$ to $R^4$ is independently hydrogen or a linear or branched alkyl group having 1 to 4 carbon atoms, X is a halogen, and
n is an integer of from 1 to 3;

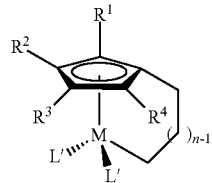

[Chemical Formula 1']

in the above Chemical Formula 1',
M is Ti, Zr or Hf,
L' is $NR^5R^6$,
each of $R^1$ to $R^4$ is independently hydrogen or a linear or branched alkyl group having 1 to 4 carbon atoms,
each of $R^5$ and $R^6$ is independently a linear or branched alkyl group having 1 to 4 carbon atoms, and
n is an integer of from 1 to 3.

\* \* \* \* \*